(12) United States Patent
Sugiki et al.

(10) Patent No.: US 11,129,944 B2
(45) Date of Patent: *Sep. 28, 2021

(54) METHOD FOR PRODUCING NEEDLE-EQUIPPED OUTER TUBE AND NEEDLE-EQUIPPED OUTER TUBE

(71) Applicant: TERUMO KABUSHIKI KAISHA, Tokyo (JP)

(72) Inventors: Tsutomu Sugiki, Yamanashi (JP); Masaaki Kasai, Yamanashi (JP); Kozo Matsumoto, Yamanashi (JP); Kenta Goto, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 246 days.

This patent is subject to a terminal disclaimer.

(21) Appl. No.: 16/269,193

(22) Filed: Feb. 6, 2019

(65) Prior Publication Data

US 2019/0167912 A1 Jun. 6, 2019

Related U.S. Application Data

(63) Continuation of application No. 14/846,597, filed on Sep. 4, 2015, now Pat. No. 10,232,128, which is a
(Continued)

(51) Int. Cl.
*A61M 5/34* (2006.01)
*A61M 5/28* (2006.01)
*A61M 5/31* (2006.01)

(52) U.S. Cl.
CPC .............. *A61M 5/343* (2013.01); *A61M 5/28* (2013.01); *A61M 5/3134* (2013.01); *A61M 5/34* (2013.01); *A61M 2005/3118* (2013.01)

(58) Field of Classification Search
CPC ........ A61M 5/343; A61M 5/349; A61M 5/34; A61M 5/0009; A61M 5/28; A61M 5/3134; A61M 2005/3118; Y10T 29/49826
See application file for complete search history.

(56) References Cited

U.S. PATENT DOCUMENTS

| 4,106,506 A | 8/1978 | Koehn et al. |
| 5,810,785 A * | 9/1998 | Bogert .................. A61M 5/343 604/264 |

(Continued)

FOREIGN PATENT DOCUMENTS

| JP | H10-113395 A | 5/1998 |
| JP | 2004-154210 A | 6/2004 |

(Continued)

OTHER PUBLICATIONS

International Searching Authority, "International Search Report," issued in connection with International Patent Application No. PCT/JP2013/056318, dated Jun. 4, 2013.
(Continued)

*Primary Examiner* — Manuel A Mendez
*Assistant Examiner* — Justin L Zamory
(74) *Attorney, Agent, or Firm* — Foley & Lardner LLP

(57) ABSTRACT

A method of manufacturing a needle-equipped outer tube includes a preheating step comprising heating a distal end connecting section to a temperature at or below a softening point of a material forming an outer tube member with a joint member inserted in a distal end connecting section of the outer tube member, and with a needle being inserted or inserted and fixed in the needle insertion hole; and a joint member welding step, performed after the preheating step, comprising thermally welding the joint member to the distal end connecting section of the outer tube member with a distal end portion of the joint member pressed toward the
(Continued)

proximal end of the joint member by a pushing member with a pressing force in a range of 4 N to 30 N.

11 Claims, 14 Drawing Sheets

Related U.S. Application Data continuation of application No. PCT/JP2013/056318, filed on Mar. 7, 2013.

(56) References Cited

U.S. PATENT DOCUMENTS

| 8,287,496 B2 | 10/2012 | Racz |
| 2002/0138042 A1 | 9/2002 | Llorach et al. |
| 2006/0167410 A1 | 7/2006 | Zeoli et al. |
| 2009/0043266 A1 | 2/2009 | Heidl et al. |
| 2009/0234288 A1 | 9/2009 | Fischer |
| 2010/0069856 A1 | 3/2010 | Sakai et al. |
| 2010/0331794 A1 | 12/2010 | Racz |
| 2012/0083749 A1 | 4/2012 | Kawamoto et al. |
| 2013/0231617 A1 | 9/2013 | Hoppe et al. |
| 2013/0296800 A1 | 11/2013 | Takemoto et al. |

FOREIGN PATENT DOCUMENTS

| JP | 2004-525687 A | 8/2004 |
| JP | 2005-342100 A | 12/2005 |
| JP | 2012-254102 A | 12/2012 |
| WO | WO-02/068027 A1 | 9/2002 |
| WO | WO-2012/034648 A1 | 3/2012 |

OTHER PUBLICATIONS

International Searching Authority, "Written Opinion," issued in connection with International Patent Application No. PCT/JP2013/056318, dated Jun. 4, 2013.

* cited by examiner

METHOD FOR PRODUCING NEEDLE-EQUIPPED OUTER TUBE AND NEEDLE-EQUIPPED OUTER TUBE

CROSS-REFERENCE TO RELATED APPLICATIONS

This application is a continuation of U.S. patent application Ser. No. 14/846,597, filed on Sep. 4, 2015, now U.S. Pat. No. 10,232,128, which is a continuation application of and claims the benefit of priority from International Patent Application No. PCT/JP2013/056318, filed on Mar. 7, 2013. The contents of these applications are incorporated herein by reference in their entireties.

BACKGROUND

Technical Field

The present disclosure relates to a needle-equipped outer tube in which a needle of a syringe is directly joined to a distal end of an outer tube of the syringe in advance, and a method of manufacturing the needle-equipped outer tube.

Background Art

In some syringes having a small volume used for insulin administration or vaccination, a needle-equipped outer tube in which a needle of the syringe is directly joined to the distal end of the outer tube of the syringe in advance is used. As a method of manufacturing such a needle-equipped outer tube, a method of joining a needle to the distal end of an outer tube with an adhesive or the like, a method of joining a needle to the distal end portion of an outer tube by insert molding, and a method of joining a needle to an outer tube by thermal welding are known (see, JP 2005-342100 A). Further, a method of pressingly inserting a cylindrical joint member, which is interpositioned between a needle and an outer tube, into the outer tube to assemble together the needle, the outer tube, and the joint member is known (see JP 2004-154210 A).

When using such a joint member, it is preferable to use a method of thermally welding the joint member to an outer tube such that, using a joint member having a tapered portion in which the outer diameter decreases from the distal end side toward the proximal end side and an outer tube including a distal end connecting section having a tapered hollow configured to receive the tapered portion of the joint member, the tapered portion is thermally welded to the tapered hollow with the joint member pressed to the outer tube toward the proximal end side of the joint member. In a thermal welding step, the entire contact surface between the joint member and the outer tube need not be thermally welded, if a thermally welded section having an annular shape is formed. In this case, a portion of the outer tube making contact with the joint member includes a non-thermal-weld section which is not heated above the softening point and is not thermally welded to the joint member.

Further, in the thermal welding step, when the entire joint member is heated above a certain degree, a distal end portion of the joint member which is not yet inserted in the tapered hollow of the outer tube softens and deforms, and thereby may increase its diameter to be larger than the inner diameter of the opening of the tapered hollow. When such deformation occurs, the deformed portion cannot advance into the tapered hollow. This makes it difficult to perform thermal welding between the surfaces of the tapered portion and the tapered hollow which are in pressed contact with each other, and thus to improve sureness of welding between the joint member and the outer tube. For this reason, it is preferable that a portion of the joint member not close to the distal end, for example a middle section, is sufficiently heated to be thermally welded in a reliable manner, but the heated area is restricted to avoid softening of the distal end portion of the joint member. Therefore, the portion of the outer tube making contact with the joint member includes a portion which makes contact but is a non-thermal-weld section. Another problem is that a portion which makes contact but is a non-thermal-weld section causes a crack after the needle-equipped outer tube is manufactured.

SUMMARY

Embodiments of the present invention are made in view of the problem. For a needle-equipped outer tube including a needle, a joint member having a needle insertion hole penetrating the joint member from the distal end to the proximal end and allowing the needle to be inserted therein and a tapered portion of which the outer diameter decreases from the distal end side toward the proximal end side, and an outer tube including a distal end connecting section having a tapered hollow configured to receive the tapered portion of the joint member, and a method of manufacturing the needle-equipped outer tube, an object of certain embodiments of the present invention is to provide a method of manufacturing a needle-equipped outer tube that can avoid generation of cracks, and a needle-equipped outer tube manufactured by that method of manufacturing.

In one embodiment, a method of manufacturing a needle-equipped outer tube including a needle, a joint member having a needle insertion hole penetrating the joint member from a distal end to a proximal end so as to allow the needle to be inserted therein and a tapered portion in which an outer diameter decreases from a distal end side toward a proximal end side, and an outer tube member including a distal end connecting section having a tapered hollow configured to receive the tapered portion of the joint member includes a preheating step comprising heating the distal end connecting section to a temperature at or below a softening point of a material forming the outer tube member with the joint member inserted in the distal end connecting section of the outer tube member, and with the needle being inserted or inserted and fixed in the needle insertion hole; and a joint member welding step, performed after the preheating step, comprising thermally welding the joint member to the distal end connecting section of the outer tube member with a distal end portion of the joint member pressed toward the proximal end of the joint member by a pushing member with a pressing force in a range of 4 N to 30 N.

In one aspect, the heating in the preheating step is performed at a temperature higher than a glass-transition point of the material forming the outer tube member.

In one aspect, the heating in the preheating step is performed at a temperature in a range of 110° C. to 150° C.

In one aspect, a material forming the joint member and the material forming the outer tube member are thermoplastic resins having compatibility with each other when melting.

In one aspect, the material forming the joint member and the material forming the outer tube member are a same thermoplastic resin or comprise a same base thermoplastic resin.

In one aspect, the material forming the joint member and the outer tube member is cyclic olefin polymer.

In another embodiment, a needle-equipped outer tube includes a needle; a joint member having a needle insertion hole penetrating the joint member from a distal end to a proximal end and allowing the needle to be inserted therein and a tapered portion in which an outer diameter decreases from a distal end side toward a proximal end side; and an outer tube member including a distal end connecting section having a tapered hollow configured to receive the tapered portion of the joint member. The joint member is disposed in the hollow of the distal end connecting section of the outer tube member and fixed to the distal end connecting section by a thermal-weld section formed at a location separated from a distal end of the distal end connecting section by a predetermined distance toward a proximal end. The distal end connecting section has a contact section, which is a non-thermal-weld section that contacts the joint member, at a location closer to the distal end than the thermal-weld section, the contact section including a residual strain but no crack.

In one aspect, the outer tube is manufactured by the method according to claim 1.

In one aspect, the contact section has a phase difference in birefringence measurement due to the residual strain, and an occurrence frequency of a phase difference exceeding 800 nm in birefringence measurement is equal to or smaller than one tenth of an occurrence frequency of a phase difference smaller than 800 nm.

In one aspect, a phase difference exceeding 900 nm does not occur in birefringence measurement in the contact section.

In one aspect, the contact section has a peak in an occurrence frequency in a range of 100 nm to 500 nm of a phase difference in birefringence measurement.

DETAILED DESCRIPTION

Figure 1:
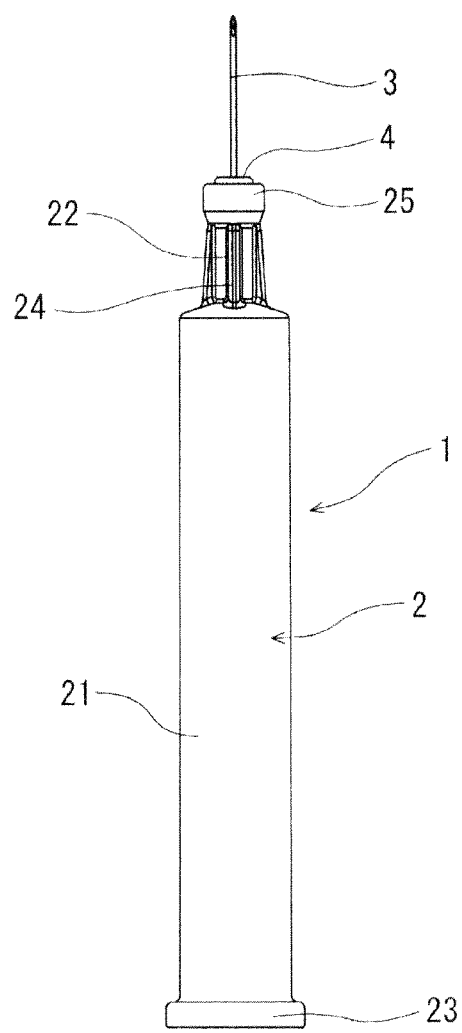
FIG. 1 is a front view of a needle-equipped outer tube according to an embodiment of the present invention.
Figure 2:
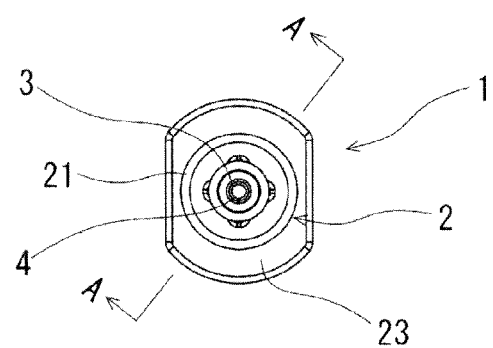
FIG. 2 is a plan view of the needle-equipped outer tube according to an embodiment of the present invention.

A needle-equipped outer tube according to embodiments of the present invention will now be described with reference to the drawings.

A needle-equipped outer tube 1 according to an embodiment of the present invention includes a needle 3, a joint member 4 having a needle insertion hole 42 penetrating the joint member 4 from the distal end to the proximal end and allowing the needle 3 to be inserted therein and a tapered portion 47 of which the outer diameter decreases from the distal end side toward the proximal end side, an outer tube member 2 including a distal end connecting section 22 having a tapered hollow 26 configured to receive the tapered portion 47 of the joint member 4.

The joint member 4 is inserted in the hollow 26 of the distal end connecting section 22 of the outer tube member 2 and fixed to the distal end connecting section 22 by a thermal-weld section 45 formed at a location away from the distal end of the distal end connecting section 22 by a predetermined distance toward the proximal end.

The distal end connecting section 22 has a contact section 46 closer to the distal end than the thermal-weld section 45. The contact section 46 is a non-thermal-weld section and makes contact with the joint member 4. The contact section 46 includes residual strain but no crack.

The needle-equipped outer tube according to the present embodiment is used for carrying out piercing from the surface of a skin with a needle tip to inject medicine into a living body.

Figure 10:
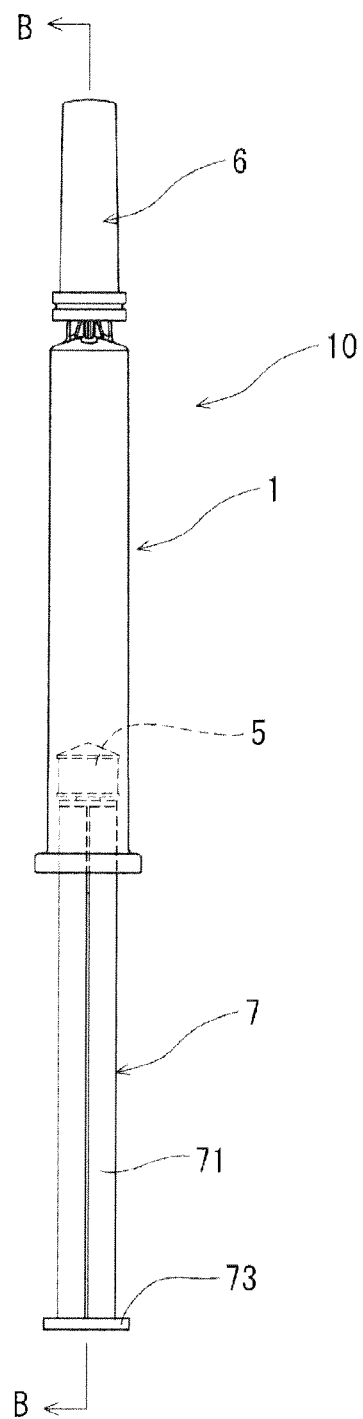
FIG. 10 is a front view illustrating a state in which a cap is attached to the needle-equipped outer tube according to an embodiment of the present invention.
Figure 11:
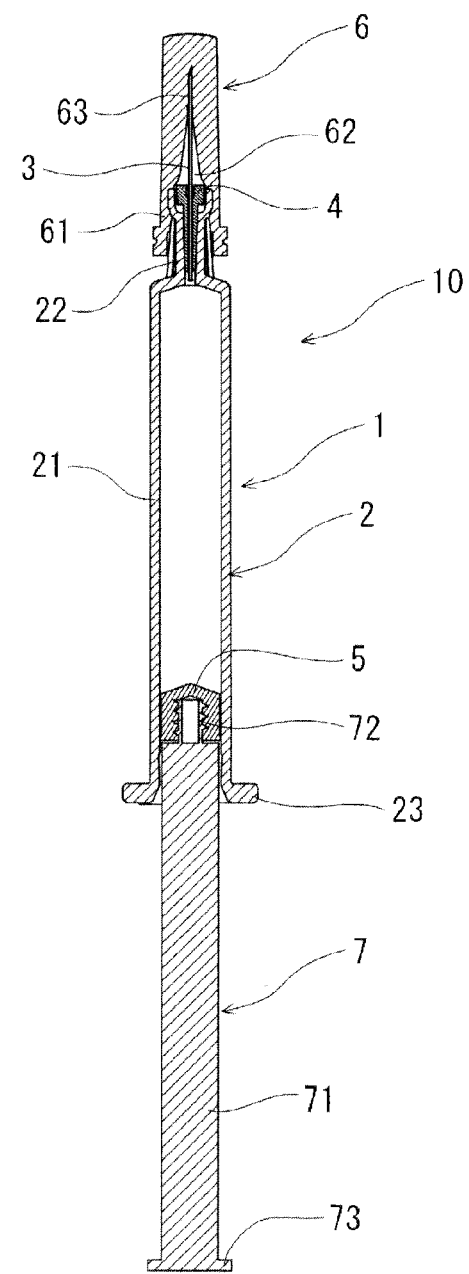
FIG. 11 is a cross sectional view of the needle-equipped outer tube illustrated in FIG. 10 taken along the line B-B.

As illustrated in FIGS. 1 to 4, the needle-equipped outer tube 1 according to the embodiment includes the needle 3, the joint member 4 to which the needle 3 is joined, and the outer tube member 2 to which the joint member 4 is joined. A cap 6 is attached to the needle-equipped outer tube 1 as illustrated in FIGS. 10 and 11.

Figure 3:
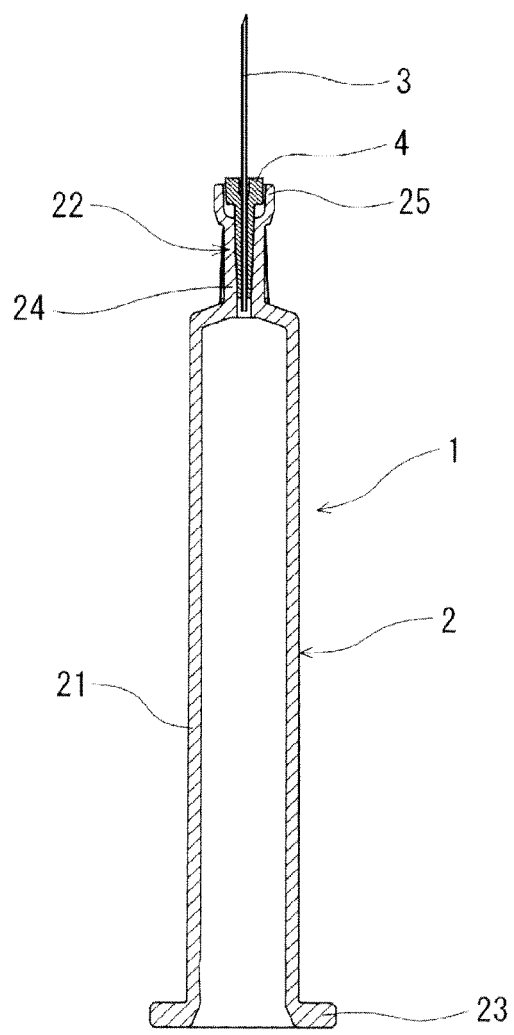
FIG. 3 is a cross sectional view of the needle-equipped outer tube illustrated in FIG. 2 taken along the line A-A.
Figure 9:
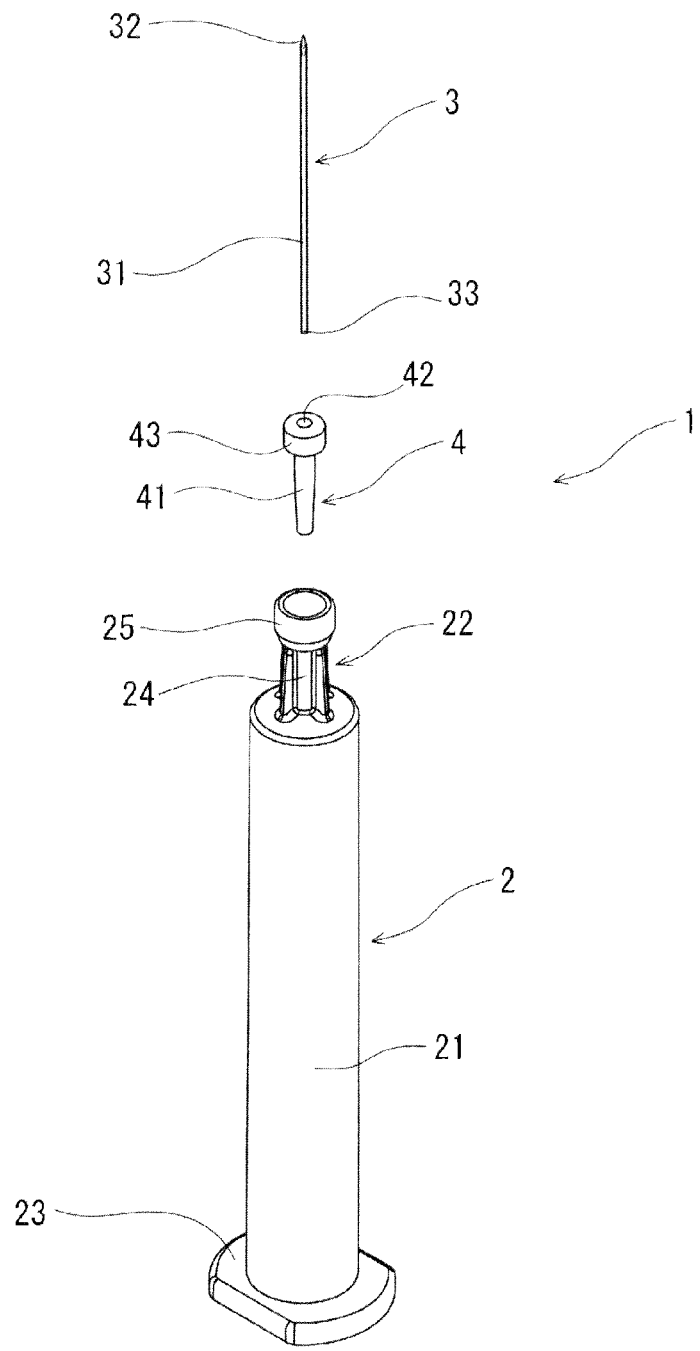
FIG. 9 is an exploded perspective view of the needle-equipped outer tube according to an embodiment of the present invention.

As illustrated in FIGS. 1, 3, and 9, a needle having a gauge size of 27 to 30 (outer diameter of ϕ0.41 to ϕ0.31 mm) according to ISO standards for medical needles (ISO9626: 1991/Amd. 1:2001(E)) is used as the needle 3.

On one end in the axial direction of the needle 3, a needle tip 32 which is to be pierced into a living body is formed. The needle tip 32 is formed to have an acute angle forming a bladed edge. The needle 3 has a length such that the needle 3 is disposed in the distal end connecting section 22, which will be described later, of the outer tube member 2 with the needle tip 32 protruding from a distal end sleeve (distal end portion) 43, which will be described later, of the joint member 4 and a proximal end 33 of the needle 3 opposite to the needle tip 32 protruding from a tapered portion 47, which will be described later, of the joint member 4.

A middle section 31 of the needle 3 is inserted in the needle insertion hole 42, which will be described later, of the joint member 4. At least the surface of the middle section 31 of the needle 3 is a rough surface roughened by blasting or the like. This enhances the joining strength between the needle 3 and the joint member 4 by the softened resin intruding into irregularities on the rough surface of the needle 3 when the needle 3 and the joint member 4 are joined by thermal welding. Furthermore, intruding of the softened resin into irregularities on the rough surface of the needle 3 can improve water-tightness.

The material of the needle 3 is preferably, for example, a stainless steel. Although, the material is not limited to a stainless steel, and may be other metal materials such as aluminum, an aluminum alloy, titanium, and a titanium alloy. Not only a straight needle, but a tapered needle at least a portion of which is tapered can be used as the needle 3. The needle 3 may have a circular cross section, or alternatively, a polygonal cross section, such as a triangular cross section. A coating material formed of, for example, a silicone resin or a fluorine-based resin may be applied to the surface of a portion of the needle 3 in the needle tip 32 side.

Figure 6:
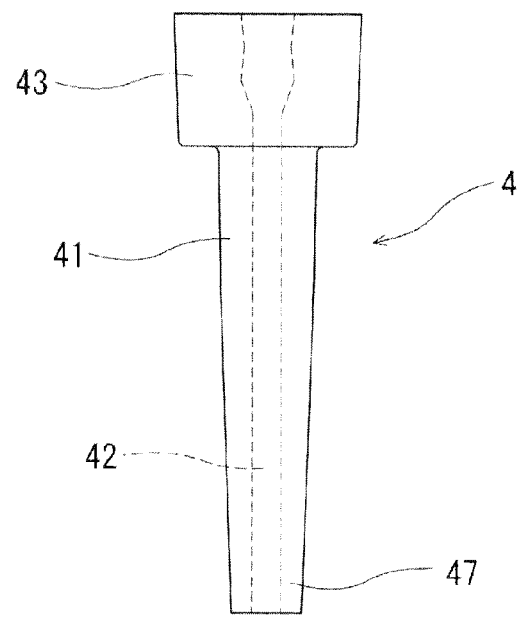
FIG. 6 is an enlarged front view of a joint member.
Figure 7:
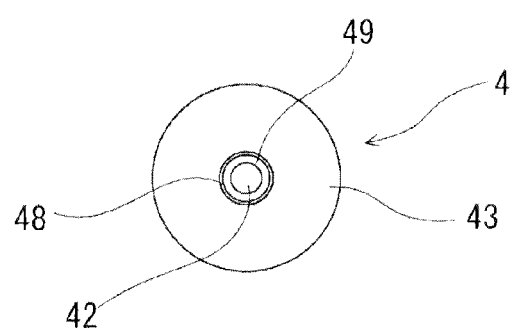
FIG. 7 is a plan view of the joint member illustrated in FIG. 6.
Figure 8:
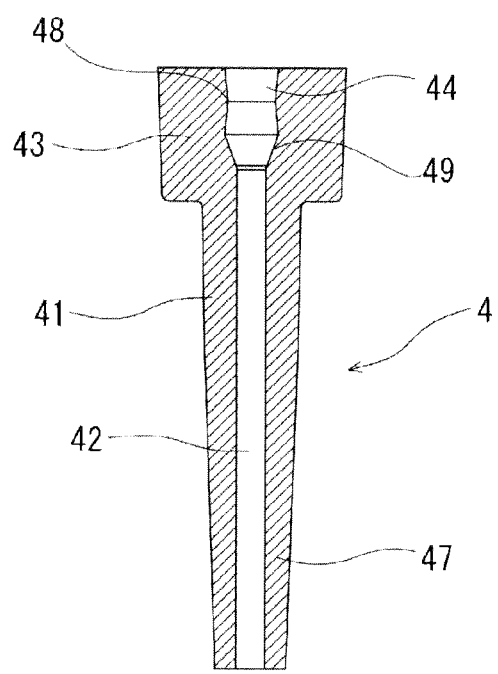
FIG. 8 is a longitudinal cross sectional view of the joint member illustrated in FIG. 6.

The joint member 4 will now be described. As illustrated in FIGS. 6 to 8, the joint member 4 is configured with the distal end sleeve (distal end portion) 43 and a proximal end sleeve 41 that is smaller in outer diameter and larger in length than the distal end sleeve 43. The distal end sleeve 43 is formed in a cylindrical shape having approximately constant outer diameter. The outer surface of the proximal end sleeve 41 composes a tapered portion 47 that is formed to have a tapered shape of which the outer diameter continuously decreases toward the proximal end side of the joint member 4. The tapered portion 47 is formed to have a radial cross section of a circular shape. In the embodiment, in particular, the cross section is formed to be an approximately true circle. As will be described later, the tapered shape of the tapered portion 47 and the tapered shape of the tapered hollow 26 of the distal end connecting section 22 of the outer tube member 2 are approximately identical. This means that the tapered portion 47 is formed to have a shape which allows almost the entire surface of the tapered portion 47 to make contact with the entire surface of the tapered hollow 26 when the tapered portion 47 is inserted in the tapered hollow 26. The tapered portion 47 is formed in a shape that can be engaged in the tapered hollow 26.

The joint member 4 is provided with the needle insertion hole 42 in which the needle 3 is inserted. The needle insertion hole 42 has an inner diameter larger than the outer diameter of the needle 3 by about 0.02 to 0.14 mm, preferably, about 0.02 to 0.11 mm. When the aforementioned needle 3 having a gauge size of 27 to 30 is used, the gap with respect to the needle 3 can be achieved as described above by providing the needle insertion hole 42 with the inner diameter of 0.43 to 0.45 mm. By determining the configuration as described above, joining strength of the joined needle 3 can be secured and tilting of the joined needle 3 at a predetermined degree or more can be prevented. The distance from the outer surface of the joint member 4 to the needle insertion hole 42, namely the thickness, is provided to be 0.38 to 0.48 mm. By using the single joint member 4 in such a configuration, the needle-equipped outer tube 1 using any of the needles 3 having a gauge size of 27 to 30 that secures joining strength of the needle 3 and prevents the joined needle 3 from tilting at a predetermined degree or more can be manufactured.

As illustrated in FIG. 8, the distal end portion of the needle insertion hole 42 (the inside of the distal end sleeve 43) is a large-diameter portion 44 having a larger diameter than the other portion. A gradually protruding annular rib 48 is formed in the portion located somewhat in the proximal end side from the distal end (opened end) of the large-diameter portion 44. The annular rib 48 has gradual inclined surface on both sides of the top of the ridge. A tapered portion 49 of which diameter decreases is provided in the proximal end side of the annular rib 48 so as to continue to the proximal end of the annular rib 48.

As materials forming the joint member 4 and the outer tube member 2, which will be described later, various types of resin such as polyvinyl chloride, polyethylene, polypropylene, cyclic olefin polymer, polystyrene, poly(4-methylpentene-1), polycarbonate, acrylic resin, acrylonitrile-butadiene-styrene copolymer, polyester such as polyethyleneterephthalate, butadiene-styrene copolymer, and polyamide (e.g., nylon 6, nylon 6,6, nylon 6,10, nylon 12) may be used. Among those, a resin such as polypropylene, cyclic olefin polymer, polyester, and poly(4-methylpentene-1) is preferably used. It is preferable that materials forming the joint member 4 and the outer tube member 2 are substantially transparent so that the inside thereof is visible.

Figure 5:
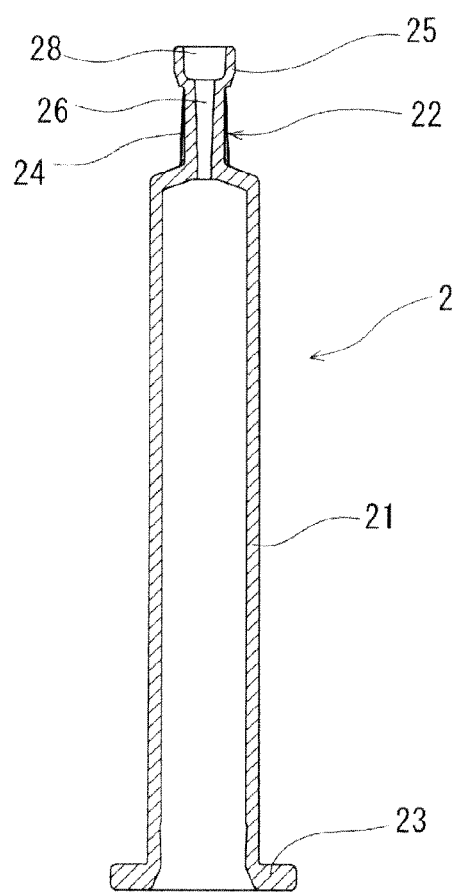
FIG. 5 is a longitudinal cross sectional view of an outer tube.

The outer tube member 2 will now be described. As illustrated in FIG. 5, the outer tube member 2 includes an outer tube body 21 which is to be filled with medicine and the distal end connecting section 22 to which the joint member 4 is joined. The outer tube body 21 is formed to have an approximately cylindrical shape including an internal container. A flange 23 is formed in the proximal end side in the axial direction of the outer tube body 21.

The distal end connecting section 22 is configured with a tapered engagement portion 24 continuing to the outer tube body 21 and a distal end engagement portion 25 continuing to the tapered engagement portion 24. The tapered engagement portion 24 is formed to have an approximately cross-shape in a radial cross section. In other words, four ribs extending along the axial direction are provided. The tapered hollow 26 which continuously increases in diameter toward the distal end and receives the tapered portion 47 of the joint member 4 described above to engage therewith by tapered surfaces is formed inside the tapered engagement portion 24. The tapered hollow 26 is formed to have a circular shape in a radial cross section. The outer tube of the embodiment, in particular, is formed to have a cross section of an approximately true circle. The thickness of the tapered engagement portion 24 where no rib exists is preferably 0.8 to 1.1 mm, more preferably, 0.9 to 1.05 mm.

Figure 4:
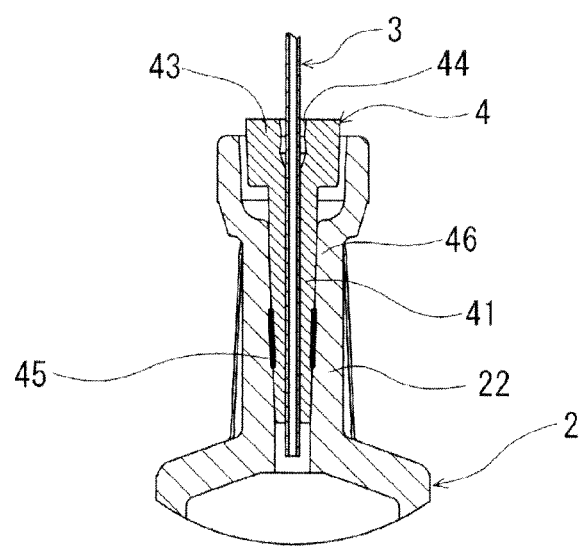
FIG. 4 is an enlarged longitudinal cross sectional view of an essential portion of the needle-equipped outer tube according to an embodiment of the present invention.

The tapered hollow 26 and the tapered portion 47 have approximately identical tapered shapes. A distal end side engagement hole 28 formed in a column shape and communicating with the tapered hollow 26 is provided inside the distal end engagement portion 25. The distal end side engagement hole 28 is formed to have a larger diameter than the tapered hollow 26. The taper angles of the tapered hollow 26 and the tapered portion 47 of the joint member 4 are not particularly limited but may preferably be 1 to 3 degrees. As illustrated in FIG. 4, the distal end side engagement hole 28 has approximately the same diameter as the distal end sleeve 43 of the joint member 4 to engage with and accommodate the distal end sleeve 43.

In the embodiment, the outer tube body 21 having an approximately cylindrical shape is exemplarily described. Although, the outer tube body 21 may be formed in a hollowed shape of a square pillar or a hexagonal pillar.

The material of the outer tube member 2 may preferably be selected from materials having compatibility with the material forming the joint member 4.

In particular, as will be described later, the distal end connecting section 22 of the outer tube member 2 is joined with the joint member 4 by thermal welding. Therefore, it is preferable that the material of the outer tube member 2 and the material of the joint member 4 are substantially the same. In this manner, preferable bondability between the distal end connecting section 22 and the joint member 4 can be obtained, so that the distal end connecting section 22 and the joint member 4 can firmly be fixed. Moreover, the welded portion between the distal end connecting section 22 and the joint member 4 can be made inconspicuous, so that aesthetic of the needle-equipped outer tube 1 can be improved.

The needle 3, the joint member 4, and the outer tube member 2 are welded by a method of manufacturing as illustrated in FIGS. 1 to 4, which will be described later, to constitute the needle-equipped outer tube 1. As illustrated in FIG. 4, the joint member 4 is fixed to the inside of the tapered hollow 26 inside the distal end connecting section 22 by the thermal-weld section 45 formed at a location away from the distal end of the distal end connecting section 22 of the outer tube member 2 by a predetermined distance toward the proximal end. The outer tube according to the present embodiment has no bubble included in and near the thermal-weld section 45. Thus no fragile portion resulting from bubbles exists.

The distal end connecting section 22 has in the distal end side of the thermal-weld section 45 the contact section 46, which is a non-thermal-weld section, which is not thermally welded but makes contact with the joint member 4. As will be described later, by having the contact section 46, which is a non-thermal-weld section, only the portion in a distal side of the joint member 4 is heated to be welded so that the portion of the joint member 4 in the side to the distal end does not soften and deform.

In the outer tube according to the present embodiment, the contact section 46 includes residual strain but no crack. The outer tube that includes the contact section 46, which is a non-thermal-weld section making contact with the joint member 4, including residual strain but no crack can be manufactured by a method of manufacturing the needle-equipped outer tube which will be described later.

Furthermore, it is preferable that the contact section 46 has a phase difference due to residual strain in birefringence measurement where the occurrence frequency of a phase difference exceeding 800 nm in birefringence measurement is equal to or smaller than one tenth of the occurrence frequency of a phase difference smaller than 800 nm. In different words, it is preferable that, in a predetermined area in a vertical cross section of the outer tube in the contact section 46, the area where a phase difference is 800 nm or larger is 10% or less than 10% of the predetermined area.

For "phase difference", an in-plane birefringence phase difference in unit thickness for incident light entering a portion of the contact section 46 along the radial direction of the distal end connecting section 22 is used. The phase difference is obtained from two types of property data, which are data on retardation (birefringence phase difference) property Re measured with a two-dimensional birefringence measuring device and data on distribution on plane of axial (phase advancing axis, phase delaying axis) angles. The phase difference (in-plane phase difference) can be measured using a commercially available phase difference measuring device (e.g., WPA-100 manufactured by Photonic Lattice Inc., KOBRA-21ADH manufactured by Oji Scientific Instruments Co., Ltd.) or by Senarmont method.

When the occurrence frequency of a phase difference exceeding 800 nm in birefringence measurement is equal to or smaller than one tenth of the occurrence frequency of a phase difference below 800 nm, the contact section 46 includes residual strain but no portion that largely deforms (for example, a crack or a portion which causes a crack).

In particular, the contact section 46 in which a phase difference exceeding 900 nm does not occur in birefringence measurement is preferable. In different words, it is preferable that a predetermined area in a vertical cross section of the outer tube in the contact section 46 substantially has no area where a phase difference is 900 nm or larger. Furthermore, the contact section 46 having a peak in occurrence frequency of phase difference within the range from 100 nm to 500 nm in birefringence measurement is preferable.

A syringe 10 using the needle-equipped outer tube 1 according to an embodiment of the present invention will now be described.

As illustrated in FIG. 10, the syringe 10 includes the needle-equipped outer tube 1 described above, the cap 6 attached to the distal end portion (needle) of the outer tube 1, a gasket 5 contained in the outer tube 1 to slide therein-side, and a plunger 7 attached to the gasket 5. The plunger 7 includes a plunger body 71, a gasket-attach portion formed in the distal end of the plunger body 71, and a pusher 73 provided in the proximal end portion. The gasket has a plunger-attach portion which receives and engages with a gasket-attach portion 72 of the plunger 7.

The cap 6 is formed in a cylindrical shape. A proximal portion 61 in the axial direction is opened and the distal end in the axial direction is closed. The cap 6 is formed of an elastic member, for example, a rubber or an elastomer. The cap 6 is attached to the distal end connecting section 22 of the outer tube member 2 so as to cover the needle tip 32 of the needle 3 and the distal end connecting section 22 of the outer tube member 2. As illustrated in FIG. 11, the needle 3 and the distal end connecting section 22 are inserted in an internal space 62 of the cap 6.

The inner diameter of the internal space 62 of the cap 6 is formed approximately identical to the outer diameter of the distal end engagement portion 25 of the distal end connecting section 22 or slightly smaller than the outer diameter of the distal end engagement portion 25. Thus when the cap 6 is attached to the distal end connecting section 22, the outer circumferential surface of the distal end engagement portion 25 makes tight contact with the inner circumferential surface of the cap 6. In this manner, the space surrounding the needle 3 protruding from the joint member 4 is sealed by the distal end engagement portion 25 and the inner circumferential surface of the cap 6. This configuration prevents adherence of germs to the needle tip 32. At the same time, the needle tip holder 63 holds the needle tip 32.

The elastic force of the inner circumferential surface of the cap 6 constricts the necked portion at the boundary between the distal end engagement portion 25 and the tapered engagement portion 24 of the distal end connecting section 22. With the inner circumferential surface of the cap 6 engaging with the necked portion of the distal end connecting section 22, the cap 6 coming off from the distal end connecting section 22 during transportation can be prevented.

A method of manufacturing the needle-equipped outer tube 1 will now be described.

The method of manufacturing the needle-equipped outer tube according to an embodiment of the present invention is of manufacturing the needle-equipped outer tube that includes the contact section 46, which is a non-thermal-weld section as described above making contact with the joint member 4, including residual strain but no crack.

In the method of manufacturing the needle-equipped outer tube according to the present embodiment, a preheating step is performed to heat the distal end connecting section 22 to a temperature at or below the softening point of a material forming the outer tube with the joint member 4 inserted in the distal end connecting section 22 of the outer tube member 2, with the needle 3 being inserted or inserted and fixed in the needle insertion hole 42, and a joint member welding step is performed after the preheating step to thermally weld the joint member 4 to the distal end connecting section 22 of the outer tube member 2 with the distal end portion of the joint member 4 pressed toward the proximal end of the joint member 4 by a pushing member 17 with a pressing force of 4 N to 30 N.

To manufacture the needle-equipped outer tube 1 according to an embodiment of the present invention, the needle 3, the joint member 4, and the outer tube member 2 are each prepared as illustrated in FIG. 9. The needle 3 is formed in a desired tubular body by, for example, press forming a sheet metal or swaging a hollow pipe. The joint member 4 and the outer tube member 2 are formed by injection molding. By separately forming the joint member 4 and the outer tube member 2, dies can be downsized and simplified.

Then an engagement step is performed to engage together the needle 3, the joint member 4, and the outer tube member 2. In the engagement step, the joint member 4 is inserted in the tapered hollow 26 and the distal end side engagement hole 28 of the distal end connecting section 22 of the outer tube member 2. When the joint member 4 is pushed in to reach the proximal end inside the distal end connecting section 22, the proximal end sleeve 41 and the tapered portion 47 of the joint member 4 engage in the tapered hollow 26 of the distal end connecting section 22 and the distal end sleeve 43 of the joint member 4 engages in the distal end engagement portion 25 of the distal end connecting section 22 of the outer tube member 2. Then an insertion step of the needle 3 is performed. In the insertion step, the needle 3 is inserted in the needle insertion hole 42 of the joint member 4, thereby assembling the needle 3 to the joint member 4 engaging with the outer tube member 2. Instead of inserting the needle 3 in the joint member 4 after the engagement step of engaging the joint member 4 in the outer tube member 2, the needle 3 may previously be inserted and fixed in the joint member 4 before performing the engagement step of the joint member 4 and the outer tube member 2.

Figure 12:
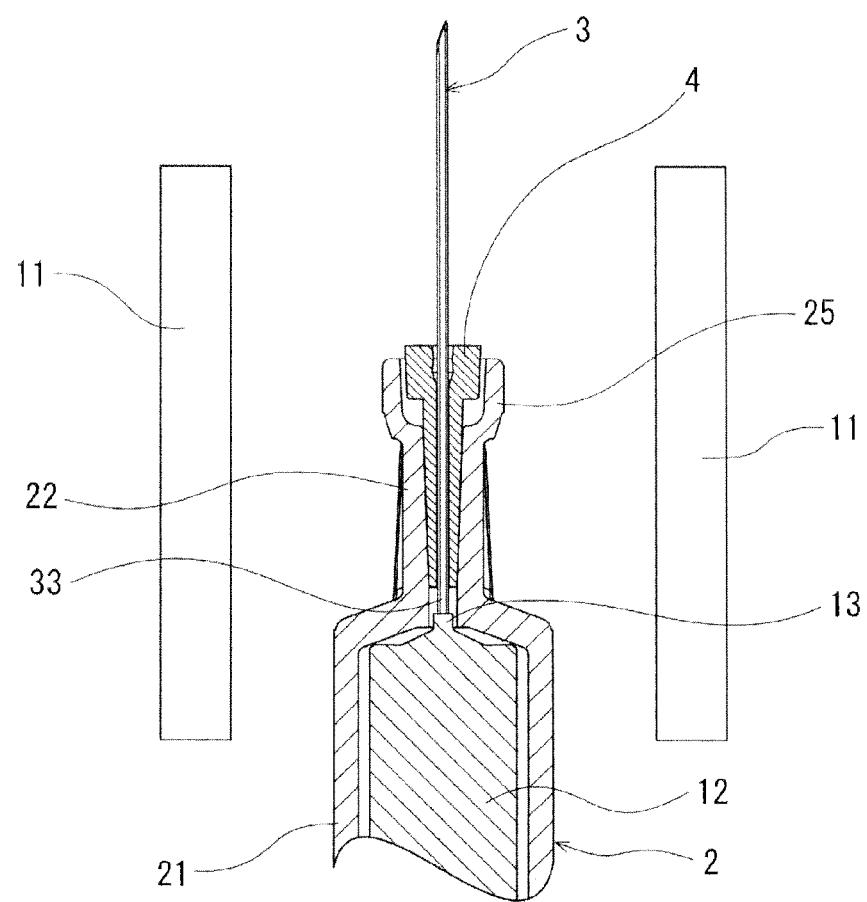
FIG. 12 is an explanatory drawing explaining preheating step in a method of manufacturing a needle-equipped outer tube according to an embodiment of the present invention.

In the embodiment as illustrated in FIG. 12, a needle supporting member 12 is used for positioning the needle 3 in the joint member 4 and the outer tube member 2. The needle supporting member 12 has on the top a supporting projection 13 to support the proximal end 33 of the needle 3 and is disposed inside the internal container of the outer tube body 21. The needle supporting member 12 is disposed so as the supporting projection 13 to be inserted in the tapered hollow 26 of the distal end connecting section 22. Thus the proximal end 33 of the needle 3 supported by the supporting projection 13 is disposed inside the distal end connecting section 22 so as the needle 3 not to protrude into the internal container of the outer tube body 21. Consequently, the dead volume inside the outer tube member 2 can be reduced, thereby reducing the amount of medicine remaining inside the outer tube member 2.

In the embodiment described above, the needle 3 provided separately from the joint member 4 is inserted in the joint member 4 after the joint member 4 engages in the distal end connecting section 22 and is positioned by the needle supporting member 12 or the like. However, this is not the only procedure. The needle 3 and the joint member 4 may previously be integrated by insert molding before the engagement step described above. In such a procedure, positioning of the needle 3 is not necessary in the joint member welding step.

Then the preheating step is performed. In the preheating step, it is preferable that heating the distal end connecting section 22 is performed to a temperature at or below the softening point of the material forming the outer tube member 2. In particular, it is preferable that heating is performed to a temperature from around the glass-transition point to the softening point of the material forming the outer tube member 2. Specifically, when the outer tube member 2 formed of cyclic olefin polymer (COP) is used, the needle-equipped outer tube 1 is preferably heated after the insertion step described above to a temperature within a range from 110° C. to 150° C.

For heating means, two halogen heaters 11 disposed in both sides of the outer tube member 2 are preferably used, as illustrated in FIG. 12. By using the halogen heaters 11, the contact section 46 of the outer tube member 2 described above can easily be heated locally. Furthermore, reaching speed of heat in the depth direction can be raised. In the example needle-equipped outer tube 1 described above, with the preheating step performed in a short period of 100 W (12 V)×2 seconds (s) can achieve the aforementioned range of heating. In the preheating step, the distal end connecting section 22 of the outer tube member 2 can uniformly be heated in circumferential direction by rotating the needle-equipped outer tube 1 about its axis. In the embodiment, the preheating step is performed for the contact section 46. Although, the preheating step may be performed for other portions where a crack might occur. Alternatively, the preheating step may be performed for the whole distal end connecting section 22.

The heating means is not limited to the halogen heater 11 described above. Other means, such as a carbon heater or hot air may be used. For example, when the needle-equipped outer tube 1 is placed inside a booth to be heated by hot air, and, for example, when the needle-equipped outer tube 1 has the same configuration as described above, the temperature is raised to be within a range from 110° C. to 150° C. by heating 290° C.×6 seconds (S) in the booth.

Figure 13:
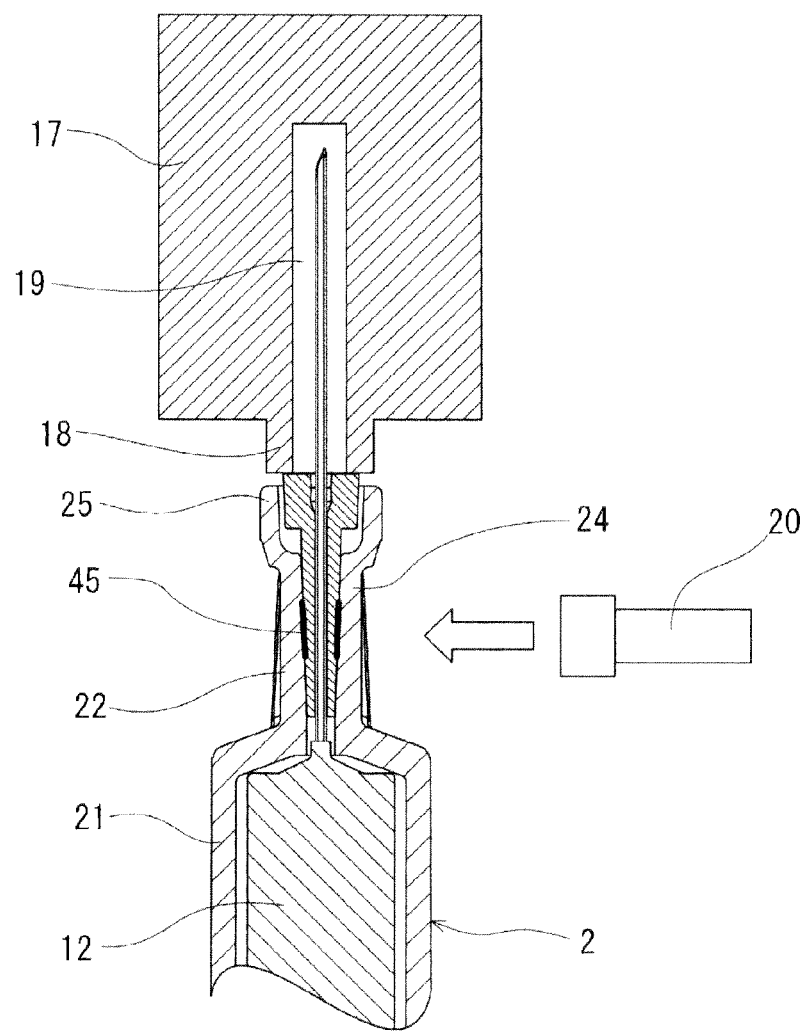
FIG. 13 is an explanatory drawing explaining joint member welding step in the method of manufacturing the needle-equipped outer tube according to an embodiment of the present invention.

Then after the preheating step, the joint member welding step is performed. As illustrated in FIG. 13, in the joint member welding step, the joint member 4 is thermally welded to the distal end connecting section of the outer tube member 2 with the distal end sleeve (distal end portion) 43 of the joint member 4 pressed toward the proximal end of the joint member 4 by the pushing member 17 with a pressing force of 4 N to 30 N.

The pushing member 17 has an accommodating hole 19 for accommodating the needle 3 and a pusher 18 for pushing the distal end sleeve 43 of the joint member 4. By applying pressure on the joint member 4 with the pusher 18, the outer circumferential surface of the tapered portion 47 and the inner circumferential surface of the tapered hollow 26 are kept in tight contact with each other in the joint member welding step, and joining strength between the joint member 4 and the distal end connecting section 22 of the outer tube member 2 can thereby be improved.

In the embodiment, thermal welding is performed by using a semiconductor laser emission apparatus 20. The semiconductor laser emission apparatus 20 irradiates the thermal-weld section 45 between the tapered portion 47 of the joint member 4 and the tapered hollow 26 of the outer tube member 2 with laser. The temperature of the needle 3 is raised and the joint member 4 is heated. The joint member 4 softens and adheres to the needle 3 and the distal end connecting section 22 of the outer tube member 2. As a result, the joint member 4 and the needle 3 as well as the joint member 4 and the distal end connecting section 22 of the outer tube member 2 are joined by thermal welding, and the needle-equipped outer tube 1 is manufactured. To achieve tight contact between surfaces of the tapered portion 47 and the tapered hollow 26 by the pushing member 17, the outer diameter of the proximal end sleeve 41 of the joint member 4 should not deform, by softening, to be larger than the inner diameter of the opening of the tapered hollow 26. Therefore, a region to be irradiated by the semiconductor laser emission apparatus is determined so that only a predetermined region in the thermal-weld section 45 close to the proximal end of the joint member 4 melts. Laser is emitted to a thin portion located between ribs of the tapered engagement portion 24.

Flexibility (deflection) of the needle can be controlled by determining the location of the thermal-weld section 45 to be at any portion. For example, to prevent kinking (bending) by adjusting the needle to deflect easily, the thermal-weld section 45 is preferably provided in a region from the middle section to the vicinity of the proximal end of the tapered engagement portion 24, or a region from the middle portion to the vicinity of the proximal end of the joint member 4. To suppress deflection, the thermal-weld section 45 is preferably provided in a region from the middle section to the vicinity of the distal end of the tapered engagement portion 24, or a region from the middle portion to the vicinity of the distal end of the joint member 4.

When the thickness of the joint member 4 is set to 0.38 to 0.48 mm, and the thickness of a portion of the tapered engagement portion 24 of the outer tube where no rib exists is set to 0.8 to 1.1 mm, it is preferable to set the output of the semiconductor laser emission apparatus 20 within a range from 5 to 20 W and the irradiation time of laser within a range from 1.5 to 2.0 seconds (s). Regarding an optical system, a focus diameter is preferably set within $\phi$3.0 to $\phi$3.5 mm. The condition described above is for a case when cyclic olefin polymer (COP) is used as the material of the joint member. The condition should be set to achieve an appropriate resin temperature according to the property of a resin to be used so as to prevent foaming, a burnt resin, and deformation. In the embodiment, the semiconductor laser emission apparatus 20 is used to join the joint member 4 and the needle 3 as well as the joint member 4 and the outer tube member 2, so that the needle 3 can be fixed to the outer tube member 2 without using an adhesive.

Furthermore in the embodiment, thermal welding is performed with the joint member 4 pressed by the pushing member 17 along the axial direction of the outer tube member 2, so that no gap is formed between the joint member 4 and the distal end connecting section 22 of the outer tube member 2. In this manner, no foaming occurs in the joint member 4 when the joint member 4 is heated. Thus the joint member 4 obtains transparency without deterioration in aesthetic, and at the same time, the joint member 4 and the needle 3 as well as the joint member 4 and the distal end connecting section 22 of the outer tube member 2 can tightly be fixed. Furthermore, an injection molded part is far smaller than that for a case where insert molding of the needle 3 is directly performed for the outer tube member 2 during injection molding of the outer tube member 2, so that a molding machine can be downsized, thereby reducing cost of facilities.

Regarding the method of manufacturing the needle-equipped outer tube 1 described above, a comparative experiment on changes in phase difference in the contact section 46 for variation of pressing forces applied to the joint member 4 by the pushing member 17 will now be described. For the needle-equipped outer tube 1 configured as described above, a phase difference in the contact section 46 of the needle-equipped outer tube 1 was measured where a pressing force applied to the joint member 4 by the pushing member 17 in the joint member welding step is 30 N (Example 1) or 10 N (Example 2). As a comparative example, a phase difference in the contact section of the needle-equipped outer tube was measured under a pressing force of 100 N. The phase difference was measured by a measuring method similar to that described above. As a result, for Example 1, in which a pressing force of 30 N was applied, the area where a phase difference is 800 nm or larger in the contact section 46 was somewhat below 10%. For Example 2, in which a pressing force of 10 N was applied, the area where a phase difference is 800 nm or larger in the contact section 46 was approximately zero. For the comparative example, in which a pressing force of 100 N is applied, the area where a phase difference is 800 nm or larger was about 30%.

Figure 14:
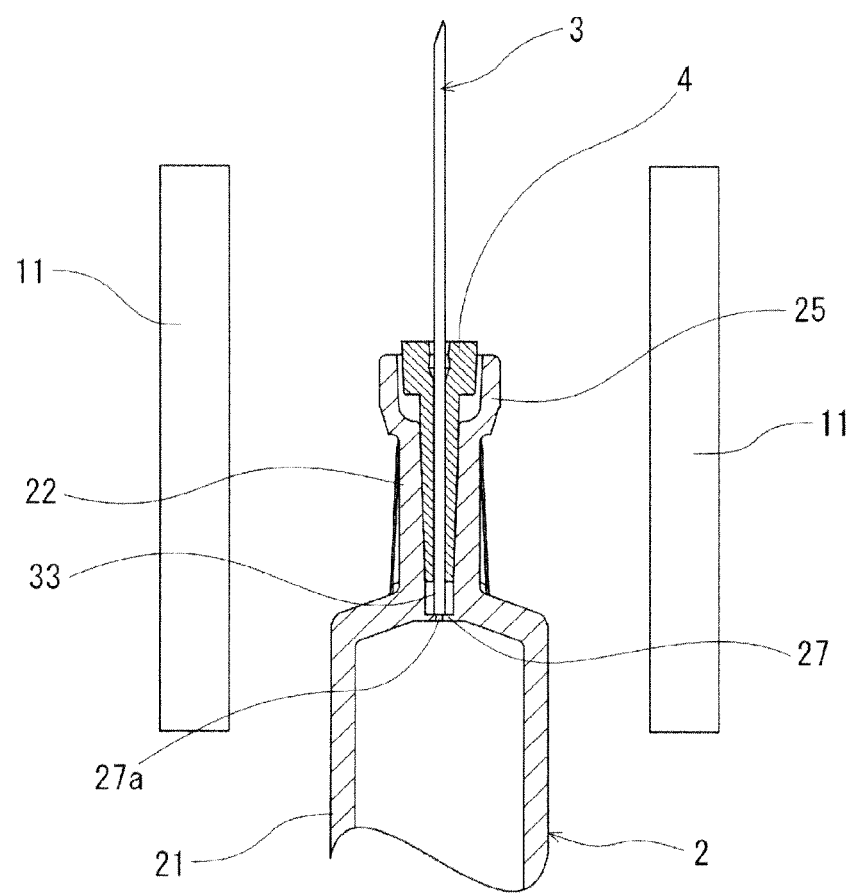
FIG. 14 is an explanatory drawing explaining a preheating step in a method of manufacturing a needle-equipped outer tube according to another embodiment of the present invention.

In the embodiment described above, the needle 3 is positioned by using the needle supporting member 12 provided separately from the outer tube member 2 in the insertion step of the needle 3. Although, the needle 3 may be positioned by a configuration different from the configuration described above. As in another embodiment illustrated in FIG. 14, for example, the needle 3 may be positioned by the needle 3 making contact with a needle stopper 27 formed inside the distal end connecting section 22 of the outer tube member 2. The needle stopper 27 is formed in a ring-shaped protrusion which protrudes from the inner surface of the tapered hollow 26. A communication hole 27a provided in the central portion of the needle stopper 27 provides communication among the internal container of the outer tube body 21, the tapered hollow 26 in the distal end connecting section 22, and the distal end side engagement hole 28. The needle hole of the needle 3 positioned by making contact with the needle stopper 27 communicates with the internal container of the outer tube body 21 via the communication hole 27a. In this manner, the needle 3 is positioned in the joint member 4 and the outer tube member 2 with the proximal end 33 of the needle 3 disposed inside the distal end connecting section 22 but not inside the internal container of the outer tube body 21. Consequently, the dead volume inside the outer tube member 2 can be reduced, thereby reducing the amount of medicine remaining inside the outer tube member 2.

Figure 15:
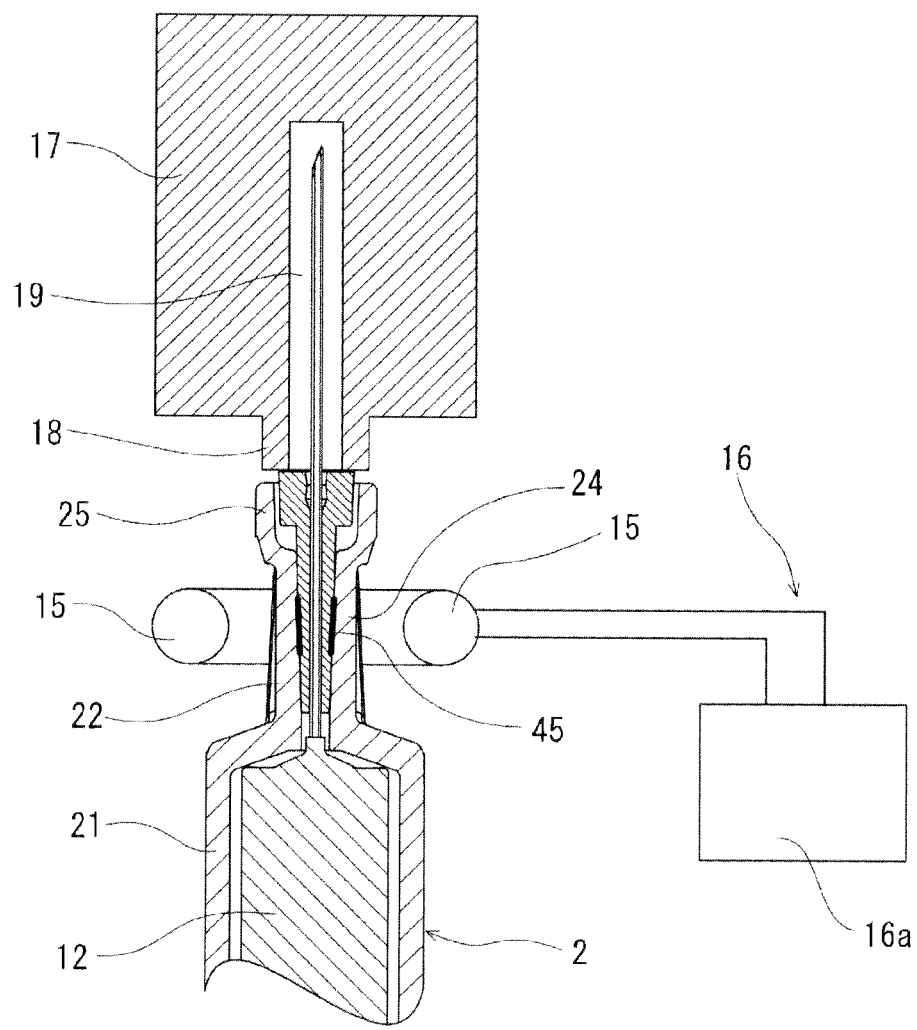
FIG. 15 is an explanatory drawing explaining a welding step of the joint member in a method of manufacturing a needle-equipped outer tube according to another embodiment of the present invention.

In the joint member welding step in the embodiment described above, welding means is not limited to the semiconductor laser emission apparatus 20 and other welding means may be used. For example, as in another embodiment illustrated in FIG. 15, a high frequency induction heating apparatus 16 may be used to carry out thermal welding. The high frequency induction heating apparatus 16 includes a work coil 15 and a power source 16a for supplying an alternative current to the work coil 15. When the power source 16a supplies an alternative current to the work coil 15, magnetic field is generated around the work coil 15 to create an eddy current in the needle 3. The temperature of the needle 3 is raised and the joint member 4 is heated. The joint member 4 softens and adheres to the needle 3 and the distal end connecting section 22 of the outer tube member 2. As a result, the joint member 4 and the needle 3 as well as the joint member 4 and the distal end connecting section 22 of the outer tube member 2 are joined by thermal welding, and the needle-equipped outer tube 1 is manufactured.

In the embodiment described above, materials being substantially the same are used for the outer tube member 2 and the joint member. Alternatively, thermoplastic resins having compatibility with each other when melting may be used as materials for the outer tube member 2 and the joint member 4. To have compatibility means to have thermodynamically good mutual solubility. In other words, two materials do not separate after solidification.

INDUSTRIAL APPLICABILITY

The method of manufacturing the needle-equipped outer tube according to an embodiment of the present invention is provided as described below.

(1) A method of manufacturing a needle-equipped outer tube including a needle, a joint member having a needle insertion hole penetrating the joint member from a distal end to a proximal end and allowing the needle to be inserted therein and a tapered portion of which the outer diameter decreases from the distal end side toward the proximal end side, and an outer tube member including a distal end connecting section having a tapered hollow configured to receive the tapered portion of the joint member, the method of manufacturing the needle-equipped outer tube including a preheating step of heating the distal end connecting section to a temperature at or below the softening point of a material forming the outer tube with the joint member inserted in the distal end connecting section of the outer tube member, with the needle being inserted or inserted and fixed in the needle insertion hole, and a joint member welding step, performed after the preheating step, of thermally welding the joint member to the distal end connecting section of the outer tube member with a distal end portion of the joint member pressed toward the proximal end of the joint member by a pushing member with a pressing force of 4 N to 30 N.

In the method according to the present embodiment, by performing the preheating step described above and selecting a low pressing force applied to the joint member in the joint member welding step, a needle-equipped outer tube having an outer tube member with no crack can easily and surely be manufactured.

Further aspects of the present embodiment are described below.

(2) The method of manufacturing the needle-equipped outer tube according to (1) described above, wherein heating in the preheating step is performed within a range from around a glass-transition point to the softening point of the material forming the outer tube member.

(3) The method of manufacturing the needle-equipped outer tube according to (1) or (2) described above, wherein heating in the preheating step is performed under a temperature from 110° C. to 150° C.

(4) The method of manufacturing the needle-equipped outer tube according to any one of (1) to (3) described above, wherein the tapered shape of the tapered portion of the joint member and the tapered shape of the tapered hollow of the distal end connecting section of the outer tube member are approximately identical.

(5) The method of manufacturing the needle-equipped outer tube according to any one of (1) to (4) described above, wherein a radial cross section of the tapered portion of the joint member is a circular shape and the radial cross section of the tapered hollow of the distal end connecting section of the outer tube member is also a circular shape.

(6) The method of manufacturing the needle-equipped outer tube according to any one of (1) to (5) described above, wherein a material forming the joint member and a material forming the outer tube member are thermoplastic resins having compatibility with each other when melting.

(7) The method of manufacturing the needle-equipped outer tube according to any one of (1) to (5) described above, wherein a material forming the joint member and a material forming the outer tube member are a same thermoplastic resin or same base thermoplastic resins having compatibility with each other.

(8) The method of manufacturing the needle-equipped outer tube according to any one of (1) to (5) described above, wherein a material forming the joint member and the outer tube member is cyclic olefin polymer.

The needle-equipped outer tube according to the present invention is provided as described below.

(9) A needle-equipped outer tube including a needle, a joint member having a needle insertion hole penetrating the joint member from a distal end to a proximal end and allowing the needle to be inserted therein and a tapered portion of which the outer diameter decreases from the distal end side toward the proximal end side, and an outer tube member including a distal end connecting section having a tapered hollow configured to receive the tapered portion of the joint member, wherein the joint member is inserted in the hollow of the distal end connecting section of the outer tube member and fixed to the distal end connecting section by a thermal-weld section formed at a location away from a distal end of the distal end connecting section by a predetermined distance toward a proximal end, and the distal end connecting section has a contact section, which is a non-thermal-weld section making contact with the joint member, in a portion closer to the distal end than the thermal-weld section, the contact section including residual strain but no crack.

Since the needle-equipped outer tube according to present invention has the contact section described above, welding is surely carried out at the thermal-weld section and no fragile portion is produced in the contact section. Thus the needle-equipped outer tube can be used in a serviceable manner.

The embodiment of the needle-equipped outer tube according to the present invention may be provided as described below.

(10) The needle-equipped outer tube according to (9) described above, wherein the outer tube is manufactured by the method of manufacturing the needle-equipped outer tube according to any one of (1) to (8) described above.

(11) The needle-equipped outer tube according to (9) or (10) described above, wherein the contact section has a phase difference due to residual strain in birefringence measurement and occurrence frequency of a phase difference exceeding 800 nm in birefringence measurement is equal to or smaller than one tenth of occurrence frequency of a phase difference smaller than 800 nm.

(12) The needle-equipped outer tube according to any one of (9) to (11) described above, wherein a phase difference exceeding 900 nm does not occur in birefringence measurement in the contact section.

(13) The needle-equipped outer tube according to any one of (9) to (12) described above, wherein the contact section has a peak in occurrence frequency within a range from 100 nm to 500 nm of phase difference in birefringence measurement.

What is claimed is:
1. A needle-equipped outer tube comprising:
a needle;
a joint member comprising a needle insertion hole penetrating the joint member from a distal end to a proxi- mal end, and a tapered portion in which an outer diameter decreases from a distal end side toward a proximal end side; and an outer tube member comprising a distal end connecting section having a tapered hollow portion configured to receive the tapered portion of the joint member, wherein the needle is located in the needle insertion hole, wherein the joint member comprises a thermally-welded section that is disposed between an inner surface of the tapered hollow portion and an outer surface of the needle at a location separated from a distal end of the distal end connecting section by a predetermined distance toward a proximal end of the distal end connecting section, wherein the joint member does not include a foamed portion.

2. The needle-equipped outer tube according to claim 1, wherein both the joint member and the outer tube member are formed of a thermoplastic resin material.

3. The needle-equipped outer tube according to claim 2, wherein both the joint member and the outer tube member are formed of the same thermoplastic resin material.

4. The needle-equipped outer tube according to claim 3, both the joint member and the outer tube member are formed of cyclic olefin polymer.

5. The needle-equipped outer tube according to claim 1, wherein the distal end connecting section has a contact section, which is a non-thermally-welded section that contacts the joint member but is not thermally welded to the joint member, at a location distal of the thermally-welded section, the contact section comprising a residual strain but no crack.

6. The needle-equipped outer tube according to claim 5, wherein the contact section has a phase difference in birefringence measurement due to the residual strain, and an occurrence frequency of a phase difference exceeding 800 nm in birefringence measurement is equal to or smaller than one tenth of an occurrence frequency of a phase difference smaller than 800 nm.

7. The needle-equipped outer tube according to claim 6, wherein a phase difference exceeding 900 nm does not occur in birefringence measurement in the contact section.

8. The needle-equipped outer tube according to claim 6, wherein the contact section has a peak in an occurrence frequency in a range of 100 nm to 500 nm of a phase difference in birefringence measurement.

9. The needle-equipped outer tube according to claim 1, wherein the thermally-welded section is disposed at a location separated from the proximal end of the distal end connecting section by a predetermined distance toward the distal end of the distal end connecting section.

10. The needle-equipped outer tube according to claim 1, wherein the joint member comprises a distal end portion having a cylindrical shape, and a proximal end portion comprising the tapered portion.

11. The needle-equipped outer tube according to claim 1, wherein the needle insertion hole comprises a distal end portion that has a larger diameter than a portion proximal of the distal end portion.

* * * * *